(12) United States Patent
Chen

(10) Patent No.: US 6,503,083 B2
(45) Date of Patent: Jan. 7, 2003

(54) INTERLOCKING IMPLANT SCREW ABUTMENT

(76) Inventor: Cyril Chen, 18 Columbia Ave., Bergenfield, NJ (US) 07621

( * ) Notice: Subject to any disclaimer, the term of this patent is extended or adjusted under 35 U.S.C. 154(b) by 0 days.

(21) Appl. No.: 09/920,228

(22) Filed: Aug. 1, 2001

(65) Prior Publication Data

US 2002/0155411 A1 Oct. 24, 2002

Related U.S. Application Data

(63) Continuation-in-part of application No. 09/839,452, filed on Apr. 20, 2001, now abandoned.

(51) Int. Cl.[7] ................................. A61C 8/00
(52) U.S. Cl. ...................................... 433/174
(58) Field of Search ................. 433/174, 172, 433/173, 201.1; 606/73

(56) References Cited

U.S. PATENT DOCUMENTS

| | | | | |
|---|---|---|---|---|
| 4,468,200 A | * | 8/1984 | Munch | 433/174 |
| 4,846,683 A | * | 7/1989 | Lazzara et al. | 433/173 |
| 5,061,181 A | * | 10/1991 | Niznick | 433/174 |
| 5,376,004 A | * | 12/1994 | Mena | 433/173 |
| 5,662,474 A | * | 9/1997 | Jorneus et al. | 433/172 |
| 5,725,375 A | * | 3/1998 | Rogers | 433/172 |
| 5,816,812 A | * | 10/1998 | Lownacki et al. | 433/174 |
| 5,879,161 A | * | 3/1999 | Lazzara | 433/173 |
| 5,984,680 A | * | 11/1999 | Rogers | 433/173 |
| 6,099,312 A | * | 8/2000 | Alvara | 433/174 |

* cited by examiner

*Primary Examiner*—Todd E. Manahan

(57) ABSTRACT

An implant screw includes a first end and a second end. A drive boss terminates a first end thereof. A first boss is formed behind the drive boss and a second boss is formed behind the first boss. A self-tapping thread is formed on a second end of the implant screw. At least one flat surface is formed along the length of the self-tapping thread. A threaded hole is formed in the first end of the implant screw. The implant abutment includes a first end and a second end. A second boss cavity is formed in the first end of the implant abutment. A first boss cavity is formed on a bottom of the second boss cavity. A drive boss cavity is formed on a bottom of the first boss cavity. A counter bore is formed through a second end of the implant abutment to receive an attachment bolt. The attachment bolt is preferably used to attach a first end of the implant screw to the first end of the implant abutment.

17 Claims, 3 Drawing Sheets

INTERLOCKING IMPLANT SCREW ABUTMENT

CROSS-REFERENCES TO RELATED APPLICATIONS

This is a continuation-in-part application taking priority from Ser. No. 09/839,452 filed on Apr. 20, 2001 now abandoned.

BACKGROUND OF THE INVENTION

1. Field of the Invention

The present invention relates generally to dental implants and more specifically to an improved interlocking implant screw and abutment for retaining a dental implant.

2. Discussion of the Prior Art

There are numerous implant screws and abutments which exist in the field. However, it appears that the junction area between the implant screw and abutment is not specifically designed to reduce micro shear movement. Further, it appears that no implant screw exists which is specifically designed to improve tapping into a jaw bone.

Accordingly, there is a clearly felt need in the art for a an improved interlocking implant screw and abutment with a junction that is specifically designed to reduce micro shear movement, and improve shear strength. There is also a clearly felt need in the art for an improved implant screw which decreases the amount of force required to tap into a jaw bone and which prevents the implant screw from rotating relative to the jaw bone once thereof is installed.

SUMMARY OF THE INVENTION

The present invention provides an improved interlocking implant screw and abutment for retaining a dental implant. The implant screw includes a first end and a second end. A drive boss terminates a first end thereof. A first boss is formed below the drive boss and has an outer perimeter which is greater in length than the drive boss. A second boss is formed below the first boss and has an outer perimeter which is greater in length than the first boss. The shape of the outer perimeters of the first and second bosses are preferably round. The drive boss preferably has a hex shape, but may be square or any other appropriate shape. A self-tapping thread is formed on a second end of the implant screw. At least one flat surface is formed along the length of the self-tapping thread. The at least one flat surface decreases the amount of force required to thread the implant screw, because there is less thread cutting surface contacting the jaw bone. The at least one flat surface also provides an area for bone fragments to collect. Further, the jaw bone will form around the at least one flat surface and prevent the implant screw from rotating in its tapped hole. A threaded hole is formed in the first end of the implant screw. The threaded hole is sized to threadably receive an attachment bolt.

The implant abutment includes a first end and a second end. A second boss cavity is formed in the first end of the implant abutment. The second boss cavity is sized to receive the second boss. A first boss cavity is formed on a bottom of the second boss cavity. The first boss cavity is sized to receive the first boss. A drive boss cavity is formed on a bottom of the first boss cavity. The perimeter around the drive boss cavity is greater at a top than at a bottom. The distance across the drive boss cavity at substantially a bottom thereof is preferably the same as the distance across the drive boss such that the outer perimeter of the drive boss contacts the bottom of the drive boss cavity. A counter bore is formed through a second end of the implant abutment to receive the attachment bolt. The attachment bolt is used to attach a first end of the implant screw to the first end of the implant abutment. Walls of the first and second boss cavities provide extra contact area for outer perimeters of the first and second bosses to improve the shear strength of the implant screw relative to the implant abutment.

Accordingly, it is an object of the present invention to provide an improved interlocking implant screw and abutment which increases shear strength between the implant screw and abutment by increasing axial contact area.

It is a further object of the present invention to provide an improved interlocking implant screw and abutment which increases shear strength between the implant screw and abutment by tapering the drive boss cavity.

It is yet a further object of the present invention to provide an implant screw which decreases the amount of force required to form a thread in a jaw bone.

Finally, it is another object of the present invention to provide an improved interlocking implant screw and abutment which provides improved transfer accuracy of the implant abutment pattern to a cap or crown.

These and additional objects, advantages, features and benefits of the present invention will become apparent from the following specification.

DETAILED DESCRIPTION OF THE PREFERRED EMBODIMENTS

Figure 3:
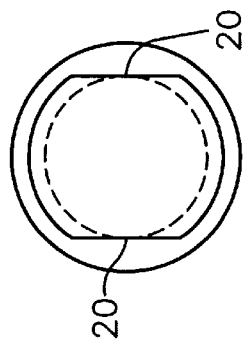
FIG. 3 is a second end view of an implant screw in accordance with the present invention.
Figure 6:
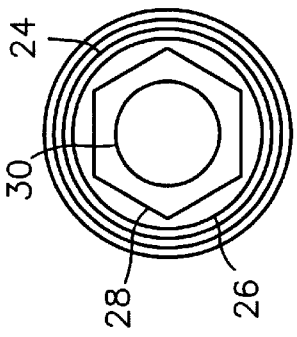
FIG. 6 is a first end view of an implant abutment in accordance with the present invention.
Figure 2:
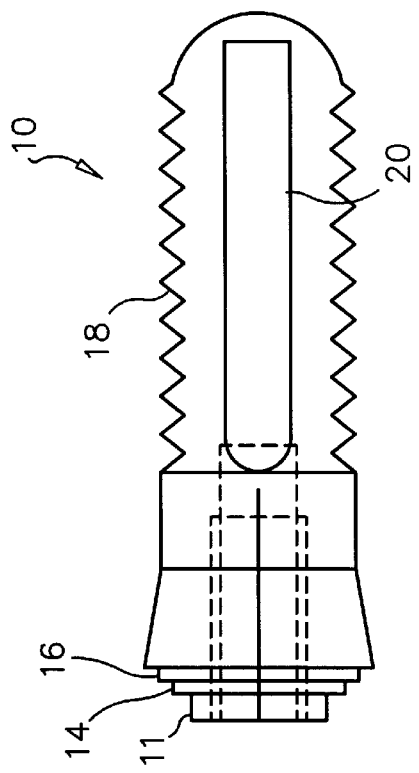
FIG. 2 is a side view of an implant screw in accordance with the present invention.
Figure 5:
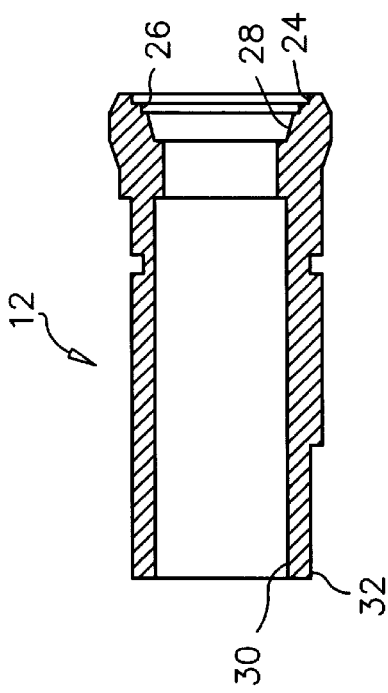
FIG. 5 is a side view of an implant abutment in accordance with the present invention.
Figure 1:
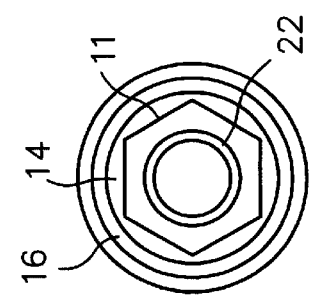
FIG. 1 is a first end view of an implant screw in accordance with the present invention.
Figure 4:
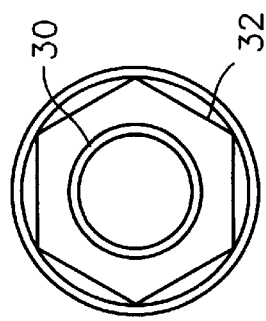
FIG. 4 is a second end view of an implant abutment in accordance with the present invention.
Figure 7:
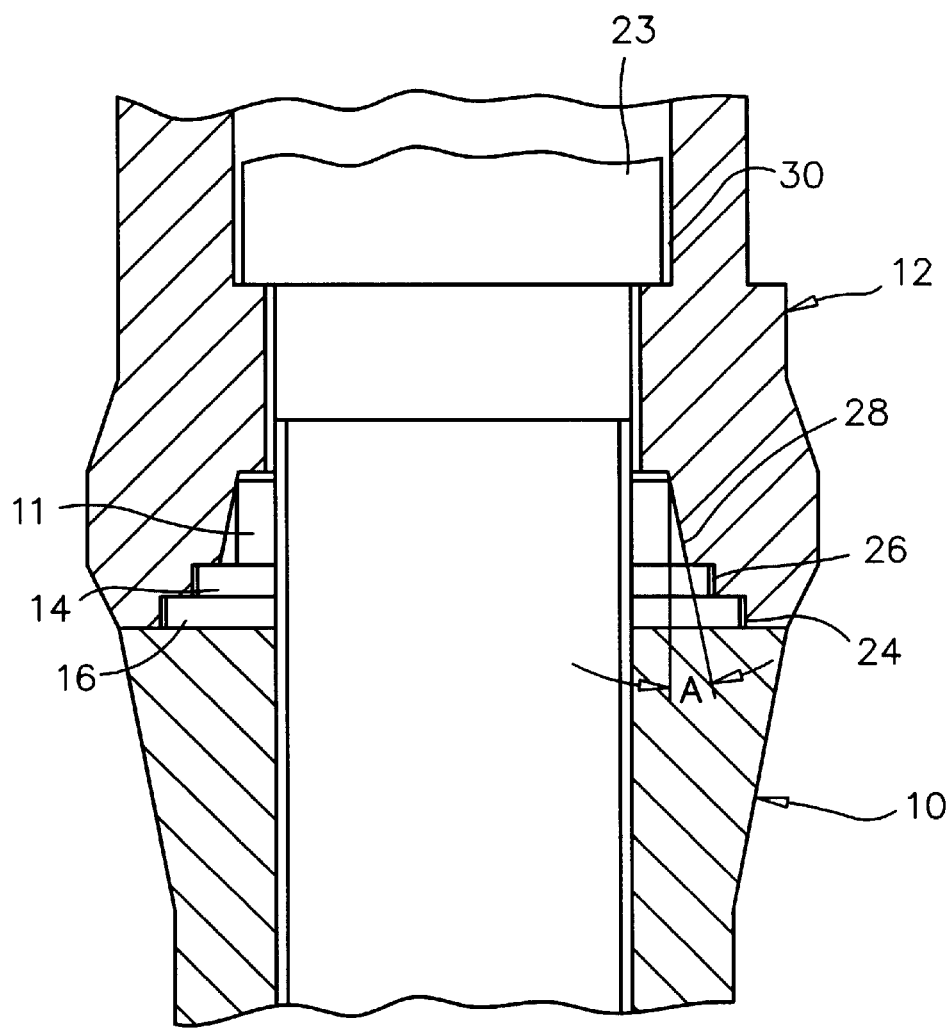
FIG. 7 is an enlarged cross sectional view of a first end of an implant screw attached to a first end of an implant abutment in accordance with the present invention.

With reference now to the drawings, and particularly to FIG. 7, there is shown an enlarged cross sectional view of a first end of an implant screw 10 attached to a first end of an implant abutment 12. With reference to FIGS. 1–3, the implant screw 10 includes a first end and a second end. A drive boss 11 terminates the first end of the implant screw 10. A first boss 14 is formed behind the drive boss 11 and has an outer perimeter which is greater than the drive boss 11. A second boss 16 is formed behind the first boss 14 and has an outer perimeter which is greater than that of the first boss 14. The shape of the outer perimeters of the first and second bosses are preferably round. The drive boss 11 preferably has a hex shape, but may be square or any other appropriate shape. A self-tapping thread 18 is formed on the second end of the implant screw 10.

Figure 8:
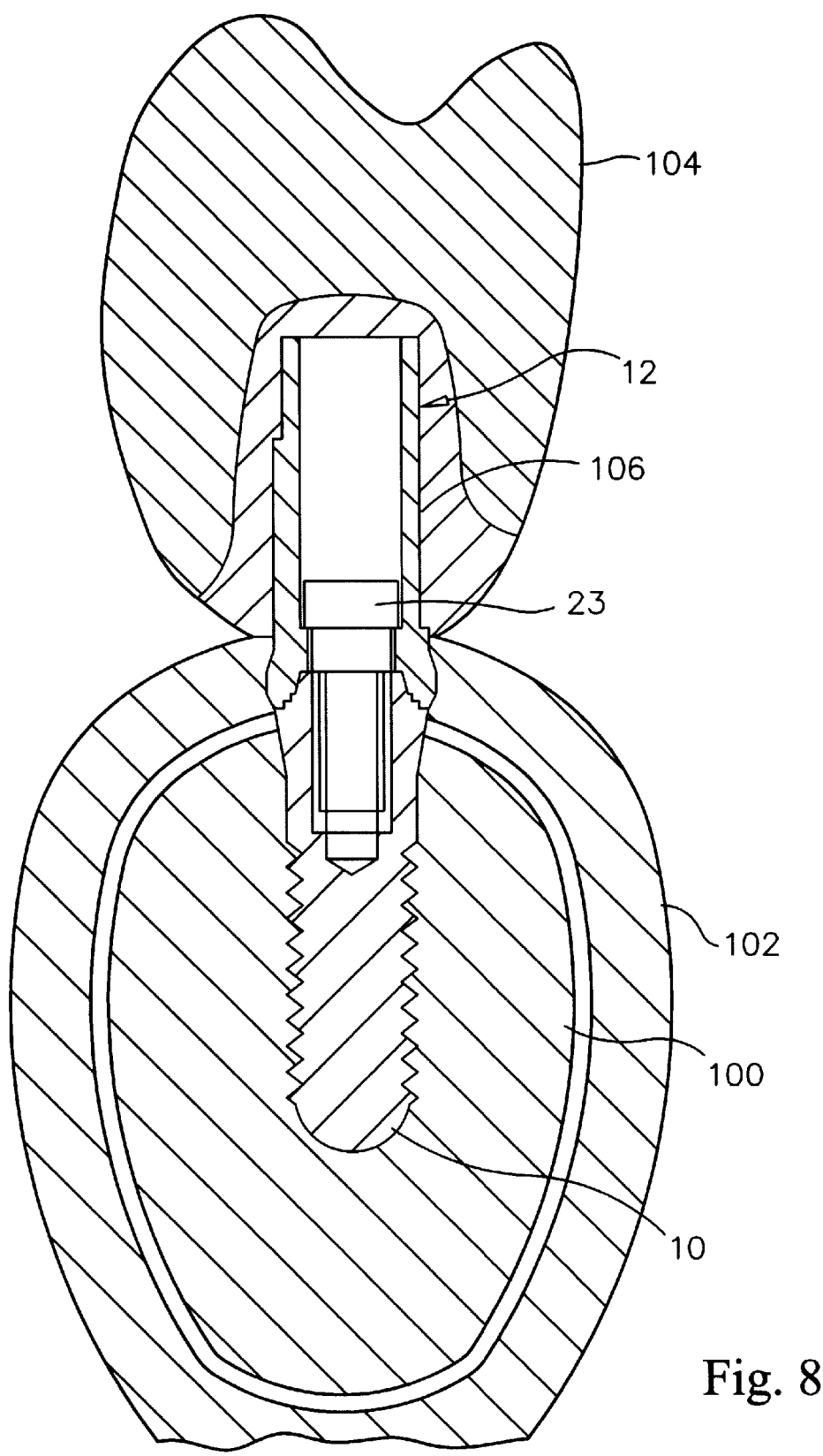
FIG. 8 is an enlarged cross sectional view of an implant screw secured to a jaw bone and a cap or crown attached to an implant abutment in accordance with the present invention.

With reference to FIG. 8, the drive boss 11 is used to rotate the self-tapping thread 18 into a hole formed in a jaw bone 100. At least one flat surface 20 is formed along the length of the self-tapping thread 18. Two flat surfaces 20 are shown in FIG. 3. The at least one flat surface 20 decreases the amount of force required to thread the implant screw 10 into the jaw bone 100, because there is less thread cutting surface contacting the hole in the jaw bone 100. The at least one flat surface 20 also provides an area for bone fragments to collect from tapping the jaw bone 100. A threaded hole 22 is formed in the first end of the implant screw 10. The threaded hole 22 is sized to threadably receive an attachment bolt 23. Further, the jaw bone 100 will heal around the at least one flat surface 20 and prevent the implant screw 10 from rotating within the tapped hole (in the jaw bone 100) when the attachment bolt 23 is tightened therein. Other means of attaching the first end of the implant screw to the first end of the implant abutment may also be used besides the attachment bolt 23.

The implant abutment 12 includes a first end and a second end. A second boss cavity 24 is formed in the first end of the implant abutment 12. The second boss cavity 24 is sized to receive the second boss 14. A first boss cavity 26 is formed on a bottom of the second boss cavity 24. The first boss cavity 26 is sized to receive the first boss 16. The clearance between the first and second bosses and the first and second boss cavities are such that when a shear force is applied to the implant abutment 12 relative to the implant screw 10, the outer perimeters of the first and second bosses contact the walls of the first and second boss cavities.

A drive boss cavity 28 is formed on a bottom of the first boss cavity 26. The perimeter around the drive boss cavity 28 is greater at a top than at a bottom. The wall of the drive boss cavity 26 flares outward from a bottom at an angle "A." The following dimension is given by way of example and not by way of limitation. Angle "A" preferably has a value of between 0.0167 degrees–5 degrees. Preferably, the distance across the drive boss cavity 28 at substantially a bottom thereof is the same as the distance across the drive boss 11 such that the outer perimeter of the drive boss contacts the drive boss cavity 28. A counter bore 30 is formed through a second end of the implant abutment 12 to receive the attachment bolt 23. The attachment bolt 23 is used to attach a first end of the implant screw 10 to the first end of the implant abutment 12. An outer perimeter 32 of the second end of the implant abutment 12 is shaped to be received a drive bit of a drive tool, such as a socket. The outer perimeter 32 preferably has a hex shape, but may be square or any other appropriate shape. The implant screw and abutment are preferably fabricated from titanium.

The implant screw and abutment are preferably used in the following manner. A hole is formed in the jaw bone 100 to receive the self-tapping thread 18. The implant screw 10 is threaded into the jaw bone 100 utilizing the implant abutment 12. After the implant screw 10 has been fully threaded into the jaw bone 100, a healing cap (not shown) is placed over the implant screw 10 and the jaw bone 100 and the gum 102 are allowed to heal. After healing, the cap is removed, and the gum 102 is cut to allow attachment of the implant abutment 12. The attachment bolt 23 is used to fasten the implant abutment 12 to the implant screw 10. The location of the implant abutment 12 is taken and transferred to a cap 104 or the like. An abutment cavity 106 is formed in the cap 104 or the like for each implant abutment 12. The cap 104 or the like is then cemented to each implant abutment 12.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

I claim:

1. An improved interlocking implant screw and abutment for retaining a dental implant comprising:

an implant screw having a first end and a second end, a drive boss terminating said first end thereof, a first boss being formed behind said drive boss, a second boss being formed behind said first boss, said first and second bosses having a round shape, a self-tapping thread being formed on a second end of said implant screw; and an implant abutment having a first end and a second end, a second boss cavity being formed in said first end thereof, a first boss cavity being formed at a bottom of said second boss cavity, a drive boss cavity being formed at a bottom of said first boss cavity, said first and second boss cavities having a round shape, attachment means for fastening said first end of said implant screw to said first end of said implant abutment.

2. The improved interlocking implant screw and abutment for retaining a dental implant of claim 1, wherein:

a top perimeter of said drive cavity having a greater length than a bottom perimeter thereof.

3. The improved interlocking implant screw and abutment for retaining a dental implant of claim 1 wherein:

said drive boss having a hex shape.

4. The improved interlocking implant screw and abutment for retaining a dental implant of claim 1, wherein:

at least one flat being formed along a length of said self-tapping thread.

5. The improved interlocking implant screw and abutment for retaining a dental implant of claim 1, further comprising:

said attachment means for fastening said first end of said implant screw to said first end of said implant abutment including a threaded hole formed in a first end of said implant screw, a counter bore formed through said implant abutment, an attachment bolt being inserted through said counter bore and tightened into said threaded hole.

6. An improved interlocking implant screw and abutment for retaining a dental implant comprising:

an implant screw having a first end and a second end, a drive boss terminating said first end thereof, a self-tapping thread being formed on a second end of said implant screw, at least one flat being formed across a width and along a length of said self-tapping thread; and an implant abutment having a first end and a second end, a drive boss cavity being formed in said first end of said implant abutment, attachment means for fastening said first end of said implant screw to said first end of said implant abutment.

7. The improved interlocking implant screw and abutment for retaining a dental implant of claim 6, wherein:

a first boss being formed behind said drive boss, a second boss being formed behind said first boss, a second boss cavity being formed in said first end of said implant abutment, a first boss cavity being formed at a bottom of said second boss cavity, and said drive cavity being formed at a bottom of said first boss cavity.

8. The improved interlocking implant screw and abutment for retaining a dental implant of claim 7, wherein:

a top perimeter of said drive cavity having a greater length than a bottom perimeter thereof.

9. The improved interlocking implant screw and abutment for retaining a dental implant of claim 7, wherein:

said first and second bosses and said first and second boss cavities having a round shape.

10. The improved interlocking implant screw and abutment for retaining a dental implant of claim 7 wherein:

said drive boss having a hex shape.

11. The improved interlocking implant screw and abutment for retaining a dental implant of claim 6, further comprising:

said attachment means for fastening said first end of said implant screw to said first end of said implant abutment including a threaded hole formed in a first end of said implant screw, a counter bore formed through said implant abutment, an attachment bolt being inserted through said counter bore and tightened into said threaded hole.

12. An improved interlocking implant screw and abutment for retaining a dental implant comprising:

an implant screw having a first end and a second end, a drive boss terminating said first end thereof, a self-tapping thread being formed on a second end of said implant screw; and an implant abutment having a first end and a second end, a drive boss cavity being formed in said first end of said implant abutment, said drive cavity continuously flaring from a bottom perimeter of said drive cavity to a top perimeter thereof, attachment means for fastening said first end of said implant screw to said first end of said implant abutment.

13. The improved interlocking implant screw and abutment for retaining a dental implant of claim 12, wherein:

a first boss being formed behind said drive boss, a second boss being formed behind said first boss, a second boss cavity being formed in said first end of said implant abutment, a first boss cavity being formed at a bottom of said second boss cavity, and said drive cavity being formed at a bottom of said first boss cavity.

14. The improved interlocking implant screw and abutment for retaining a dental implant of claim 12, wherein:

at least one flat being formed along a length of said self-tapping thread.

15. The improved interlocking implant screw and abutment for retaining a dental implant of claim 13, wherein:

said first and second bosses and said first and second boss cavities having a round shape.

16. The improved interlocking implant screw and abutment for retaining a dental implant of claim 13 wherein:

said drive boss having a hex shape.

17. The improved interlocking implant screw and abutment for retaining a dental implant of claim 13 further comprising:

said attachment means for fastening said first end of said implant screw to said first end of said implant abutment including a threaded hole formed in a first end of said implant screw, a counter bore formed through said implant abutment, an attachment bolt being inserted through said counter bore and tightened into said threaded hole.

* * * * *